| United States Patent [19] | [11] Patent Number: 4,668,359 |
| Postle et al. | [45] Date of Patent: May 26, 1987 |

[54] DIAGNOSTIC STRIP

[75] Inventors: Stephen R. Postle, Wilmslow; Peter J. Elton, Macclesfield; David P. Gregory, Wilmslow; Janice Butcher, Goostrey, all of England

[73] Assignee: Ciba-Geigy AG, Basel, Switzerland

[21] Appl. No.: 861,677

[22] Filed: May 9, 1986

[30] Foreign Application Priority Data

May 24, 1985 [GB] United Kingdom ................ 8513152

[51] Int. Cl.$^4$ ................................................ B01K 5/00
[52] U.S. Cl. .............................. 204/182.7; 106/208; 204/183.1; 204/299 R; 424/2; 427/8; 427/39; 427/40; 427/41; 436/516
[58] Field of Search ...................... 436/516; 424/2, 37; 427/39, 40, 41, 8; 204/299 R, 183.1, 182.7, 182.8; 106/208

[56] References Cited

U.S. PATENT DOCUMENTS

| 3,527,712 | 9/1970 | Renn et al. | 106/208 |
| 3,578,604 | 5/1971 | Uriel | 204/299 R |
| 3,896,021 | 7/1975 | Fosslien | 204/182.7 |
| 4,006,069 | 2/1977 | Hiratsuka et al. | 436/516 |
| 4,290,911 | 9/1981 | Cook et al. | 436/516 |
| 4,548,869 | 10/1985 | Ogawa et al. | 204/299 R |
| 4,548,870 | 10/1985 | Ogawa et al. | 204/299 R |
| 4,576,689 | 3/1986 | Makkaeu et al. | 427/42 |
| 4,576,831 | 3/1986 | Hosol et al. | 427/40 |

Primary Examiner—Arthur P. Demers
Attorney, Agent, or Firm—Wenderoth, Lind & Ponack

[57] ABSTRACT

A diagnostic strip which comprises a base having coated thereon a dried layer which has been formed by coating onto the base an aqueous solution which comprises from 0.5 to 2.0% by weight of agarose and from 0.5 to 3.0% by weight of non-cross linked polyacrylamide or polyvinyl alcohol or a mixture of these polymers, the dried layer being 0.1 to 100 μm thick and comprising 10 to 50% by weight solids.

16 Claims, No Drawings

DIAGNOSTIC STRIP

The present invention relates to strip material of use in electrophoresis and similar techniques such as immunoelectrophoresis, affinity electrophoresis and iso-electric focusing. Such strips are hereinafter referred to as diagnostic strips even though they may be used in preparation techniques.

Agarose, a polysaccharide derived from agar-agar, itself derived from seaweed, has been used as a medium in which to effect such electrophoretic separations. Agarose forms like agar-agar a stiff jelly when dissolved in water and dried. Kits for preparing agarose plates have been available for some years, such kits include agarose powder and dishes in which to form the agarose jelly. Likewise agarose cast onto glass plates with a coating thickness of about 0.5 mm have also been available. However, preparation of agarose in dishes using a kit is both time consuming and expensive. On the other hand comparatively thick layers of agarose precast on glass plates are even more expensive. Thus the use of agarose has been severely restricted. However we have found novel diagnostic strips coated with a thin coating which includes agarose which are easy to prepare in large quantities, which can then be dried for ease of handling, but which when soaked in water or in a buffer solution can then reswell to provide a medium which can be used in electrophoresis and similar techniques.

Certain prior art patent specifications describe elements for electrophoresis which comprise a minor amount of agarose in the coating. These are U.S.P. at No. 3,578,604 and European patent applications 126638 and 126639. But in all these prior proposals the main medium for electrophoresis is cross-linked polyacrylamide. A certain amount of agarose or other water-soluble polymer is present to modify the properties of the cross-linked polyacrylamide in the assemblies described in these patent specifications. However cross-linked polyacrylamide layers are formed by mixing straight-chain polyacrylamide with a cross-linking agent such as methylene bis-acrylamide and coating the mixture on a base in the absence of oxygen. A comparatively thick cross-linked polyacrylamide gel is then formed. If this gel is dried down several hours swelling are then required to reswell the gel to enable it to be used for electrophoresis. Great trouble has been experienced in obtaining cross-linked polyacrylamide layers by this method which are not too brittle to handle and which adhere well to the base on which they have been coated.

According to the present invention there is provided a diagnostic strip which comprises a base having coated thereon a dried layer which has been formed by coating on the base an aqueous solution which comprises from 0.5 to 2.0% by weight of agarose and 0.5% to 3% by weight of non-crosslinked polyacrylamide or of polyvinyl alcohol or of a mixture of these polymers, the dried layer being 0.1 to 100 μm thick and comprising 10 to 50% by weight of solids.

According to another aspect of the present invention there is provided a method of preparing a diagnostic strip coated with agarose which comprises preparing a roll of web material so that an aqueous gelatino silver halide emulsion can adhere thereto on one side thereof, but which does not have a gelatin or any other proteinacious layer on the prepared side, then coating on the prepared side of the web by a continuous web coating method a layer of an aqueous solution which comprises from 0.5 to 2% by weight of agarose and from 0.5 to 3.0% by weight of non-cross-linked polyacrylamide or of polyvinyl alcohol or of a mixture of these polymers at a temperature of at least 40° C., drying the coated agarose and polymer layer to provide a dried layer 0.1 to 100 μm thick and comprising 10 to 50% by weight of solids and cutting the coated web into strips of the required size.

Preferably, the thickness of the dried layer is from 5.0 to 15 μm.

Preferably the percentage of solids in the dried layer is from 15 to 30, and most preferably about 20% by weight.

If the percentage of liquid in the coating solution is above 50% the layer is tacky and cannot be handled without damage because it cannot be dried properly. If the percentage of solids is below 10% then the dried layer when soaked in water followed by a buffer, which is the preferred method of reconstituting the layer before use, will not reconstitute correctly and thus the material cannot be used for any of the techniques hereinafter listed.

The inventively used polyacrylamide preferably comprises a straight chain polyacrylamide having a molecular weight below 100.000 together with a minor portion of a straight chain polyacrylamide having a molecular weight over 400.000. More preferably, it comprises a straight chain polyacrylamide having a molecular weight of from 30.000 to 100.000 together with a minor portion having a molecular weight from 400.000 to 600.000.

The web material may be a web of paper material which has been sized to retard the absorbtion of water into the base the sizing agent used being non-proteinacious, but being sufficiently hydrophilic in nature to allow the web to be coated with an aqueous gelatino silver halide emulsion. The web material may be polyethylene laminated paper wherein one side has been corona discharged treated so as to render this side receptive to an aqueous gelatino silver halide emulsion layer.

Preferably, however, the web material is a film material of the type used as a film base of photographic films, but which has no gelatin subbing layer. Such a film material may be cellulose triacetate or cellulose acetate-butyrate which has been treated to make it receptive to an aqueous gelatino silver halide emulsion layer.

Most preferably the web material is a polyester film material which has been prepared by a process wherein the unorientated polyester in webform is orientated in one direction in a stentor, a latex copolymer is then coated on one surface at least of the polyester, orientation of the polyester in the other direction is completed together with a heat-setting procedure. In some cases a corona-discharge treatment of the coated polymer surface is then carried out. Thereafter the agarose and polymer solution is coated on the copolymer surface of the biaxially orientated polyester film.

Most preferably the copolymer used comprises up to 10% by weight of itaconic acid.

Suitable copolymers for use in this method are described in British patent specification Nos. 1,540,067, 1,583,343 and 1,589,926. In methods described in these specifications corona discharge treatment of biaxially orientated polyester is required to obtain the best adhesion after an aqueous coating solution layer has been applied.

Another suitable copolymer is described in British patent No. 1,571,583 but in this case no corona discharge treatment of the copolymer layer is required to render the surface receptive to an aqueous coating solution layer.

Most preferably the copolymer is a styrene based copolymer.

Coatings having a dried thickness of over 100 μm could also be prepared by this method but such coatings are unnecessarily wasteful in agarose because coatings as thin as 5 to 15 μm have been found to function very well as diagnostic strips and require a shorter re-swell period.

Various additives may be added to the agarose and polymer solution before it is coated. Such additives include wetting agents as coating aids. Humectants for example glycerol, which help to plasticise the coated layer. Bacteriocides for example phenol to improve the shelf life of the coated strips. Additives for example sorbitol and galactomannan which help to improve the water-solubility of the agarose may also be used.

The strips prepared by the method of the present invention are treated in a liquid before use to swell the agarose and polymer layer. This liquid is usually water or a selected aqueous buffer. To aid the swelling of the agarose and polymer layer additives for example urea may be added to the agarose and polymer coating solution, optionally together with ampholytes which are mentioned below.

Agarose is a purified linear galactan hydrocolloid solid which is isolated from agar or recovered directly from agar bearing marine algae. Different agarose preparations vary significantly with respect to their physical and chemical properties.

Agarose alone when used in kit form or when cast in thick layers on plates is satisfactory to be used for electrophoretic separations because in the first case the agarose powder is mixed with the usually required buffer and in the second case the buffer is present in the partially dried down thick layer. However when layers of agarose alone are coated on a roll of web material and the layer dried insufficient buffer or water is taken-up by the dried agarose to allow electrophoretic separation to be achieved. The drying of the thin agarose layer seems to collapse in some way the structure of the agarose. However in the diagnostic strip of the present invention when a polymer of the type as herein before defined is present as well in the layer the desirable structure of the agarose coating is reconstituted when the dried coating is rehydrated in water or preferably in a selected buffer solution. This reconstituted layer can be used for electrophoresis and similar techniques. The swell time to reconstitute the layer before use can be as short as 0.5 hours compared with the prior art materials which often require a swell time of a few hours.

Thus the most important part of the rehydrated coating is the agarose and its gel strength, porosity and electroendosmosis properties. Porosity, particularly is adversely affected by drying the coating layer unless the specified polymer is also present in the coated layer.

The physical and chemical properties of the agarose are influenced by the source of seaweed, including location and stage of growth cycle, the recovery procedure and the process used to isolate the agarose.

Properties of the agarose such as gelling temperature, gel strength, porosity and electroendosmosis can be adjusted by blending two or more batches. The gelling and melt temperatures are related to the methoxyl content of the agarose and properties of agarose can be influenced by incorporating hydroxy ethyl groups; e.g. Miles Seaplaque Agarose. Agarose gels are not absolutely clear due to regions of microcrystallinity. Low concentrations of urea and polyethylene glycol reduce turbidity but gel strength is reduces. Although predominantly neutral the agarose and polymer matrix contains some anionic residues, e.g. sulphate and pyruvate, associated with those residues are hydrated counter ions. When an electric current is applied counter ions migrate towards the cathode carrying water of hydration and any neutral sample molecules with them, this is known as electroendosmosis. This is beneficial in counter electrophoresis diagnostic techniques, though not in Isoelectric Focusing. Isoelectric Focusing takes advantage of the fact that each protein has a different pH at which it is electrically neutral; its isoelectric point (pI). Proteins are separated according to pI by electrophoresis on a gel in which a stable pH gradient has been generated by incorporation of ampholytes. Ampholytes can be mixtures of amides and carboxylic acid groups which come to rest in order of pI when subjected to an electric field and each of which maintains a local pH corresponding to its pI by virtue of a strong buffering capacity. The ampholytes can be incorporated during formulation or in swelling of the dried agarose and polymer layer and with little effect of degree of separation achieved.

Many other electrophoretic and immunology, cell culture and cloning techniques can be used with agarose and polymer layers having varying physical and chemical properties, e.g. serum protein electrophoresis, nucleic acid electrophoresis, separation by molecular weight, 2D electrophoresis, cell and virus electrophoresis, Ouchterlony gel diffusion, radial immunodiffusion, immunoelectrophoresis, Laurell rockets and crossed immunoelectrophoresis, counter electrophoresis and antigen antibody overlays.

When the coated agarose and polymer strips are to be used for iso-electric focusing ampholytes for example mixtures of compounds which contain amide and carboxylic acid groups may be added to the agarose and polymer solution. However, preferably ampholytes are added to the swelling liquid.

Continuous web coating machines which can be used to coat the agarose and polymer solution onto the web include any of the coating machines used to coat size solutions onto paper web and any of the machines used to coat gelatin solutions onto photographic base materials. Such coating machines include slot and through coating machines with or without air blade or doctor bar layer thickness controlling devices. Also cascade and curtain coating machines may be employed as well as gravure and reverse gravure coating machines.

The agarose and polymer aqueous solution may be prepared by adding the requisite amount of agarose powder to water and allowing the mixture to stand for one hour. The mixture is then heated rapidly with efficient stirring to above 50° C. and held at the elevated temperature for 30 minutes or until all the powder has dissolved. This is shown by a considerable reduction in turbidity of the solution. The temperature is then lowered with constant stirring to 5° C. above the desired coating temperature and the polymer then added to the agarose solution. The solution is then placed in a thermostated storage vessel until it is coated. The actual coating temperature above 40° C. depends on the type of agarose used and on the use of the diagnostic strips.

The dried agarose and polymer layers can easily be swollen by soaking in a suitable solvent. The degree of swelling is dependent on the type and quantity of agarose coated, the amount and type of polymer used, the temperature of swelling, the type and pH of the solvents used. Agarose and polymer coatings for electrophoretic techniques are soaked in a dilute form of the buffer to be used in the protein separation.

It is an important feature of the strips prepared by the method of the present invention that no gelatin subbing layer be present between the polyester base and the agarose and polymer layer.

As gelatin is protein based this interferes greatly with protein separation techniques. In the preferred method of the present invention the dried latex styrene based copolymer applied at the interdraw stage provides a hydrophilic layer onto which the agarose and polymer coating solutions can be applied and to which it can adhere. Preferably the film base after full orientation and heat setting is corona discharge treated. This adds to the adherence of the agarose and polymer solution to the base. However it is not always necessary.

The following Examples will serve to illustrate the invention:

EXAMPLE 1

A polyester polyethylene terephthalate film base support prepared as described in Example 11 of British patent specification no. 1,540,067, except that no silver halide emulsion was coated onto the corona discharge treated film surface, was used.

An agarose aqueous solution was prepared as follows:
Agarose (Miles Medium EEO): 18.75 g
Allied Colloids Straight Chain
Polyacrylamide average MW 44,000 (20% aqueous sol.): 150 g (30g)
Polyacrylamide average MW 500,000 (12.5% aqueous sol.): 12 g (1.5 g)
Wetting Agent (Olin 10G 10% aqueous sol.): 7.5 g
water: 1315.5 g
Total: 1500 g The agarose was soaked in water for 60 minutes with stirring in the presence of the wetting agent. The mixture was heated strongly with vigorous stirring until it boiled at 96° C. The temperature was lowered to 92° C. and maintained at this temperature until an opaque appearance was obtained. The temperature of the solution was reduced to 65° C. and the polyacrylamide solutions added, whilst stirring constantly.

The agarose and polyacrylamide solution was then transferred to a thermostated coating vessel. The solution was then slot coated onto the polyester film base as just described. The film base was carried past the coating slot at 15 feet per minute and the volume per unit area of solution coated on the film base was 2.1 $cm^3 dm^{-2}$. The temperature of the coating solution when coated was 60° C.

The coating was then chilled to set the agarose and polyacrylamide and air impingment dried. The thickness of the coated dried agarose layer was 10 µm.

The film base coated with dried agarose and polyacrylamide layer was then chopped into strips 5 x 8 cm in length which is a suitable size for diagnostic strips.

Both wet and dry adhesion tests as described in British Patent No. 1,540,067 were carried out and in both tests the agarose layer adhered very well to the film base.

One of these strips was used in an electrophoresis test to show what proteins were present in a sample of human serum. A Shandon 600 Electrophoresis Chamber was employed.

The strip was then submerged in 200 ml of distilled water for 10 minutes and then drained.

The strip was then placed in an aqueous buffer bath (pH 8.6 0.1M) (known as a Barbital bath) for 20 minutes to swell the agarose and polyacrylamide layer. Excess buffer was removed and the strip placed in the electrophoresis chamber, each end of the strip dipping into a bath of 0.05M buffer.

A small volume of the serum was applied to one end of the strip using a commercially available applicator. Small samples containing known serum proteins were placed in a line along the strip at the same end.

A constant current of 4mA which is 4MA/5 cm width of strip was applied for 25 minutes. The agarose and polyacrylamide strip was then removed from the chamber and placed in a concentrated Coomassie Blue solution in 5% acetic acid tostain the proteins.

Adventitious staining was then removed by soaking in acetic acid/methanol/water for ten minutes, leaving only the separated proteins stained.

The strip was then dried.

The dried strip showed the various proteins present in the serum sample separated along the length of the strip. Their identity was established by comparison with known proteins which had also been separated along a comparison strip.

This test shows that the strips prepared by the present invention even though the coated layer of agarose and polymer was very thin are of use in an electrophoresis protein separation technique.

In this example the small amount of higher molecular weight polyacrylamide was used to increase the viscosity of the coating solution to enable a suitable coating weight of agarose and polymer to be obtained.

EXAMPLE 2

A strip was prepared in exactly the same manner as in Example 1 except that instead of the polyacrylamide solutions being added to the agarose solution 30 g of polyvinyl alcohol (100% hydrolysis) having a molecular weight of 14000 was used. The strip was soaked in water and then in buffer as in Example 1 and a similar electrophoretic test was carried out. As in Example 1 various proteins present in the serum sample separated along the strip. This showed that the strip was useful in an electrophoresis protein separation technique.

We claim:

1. A diagnostic strip which comprises a base having coated thereon a dried layer which has been formed by coating onto the base an aqueous solution which comprises from 0.5 to 2.0% by weight of agarose and from 0.5 to 3.0% by weight of non-cross linked polyacrylamide or polyvinyl alcohol or a mixture of these polymers, the dried layer being 0.1 to 100 µm thick and comprising 10 to 50% by weight solids.

2. A strip according to claim 1 wherein the thickness of the dry layer is from 5.0 to 15.0 µm.

3. A method of preparing a diagnostic strip coated with agarose which comprises preparing a roll of web material so that an aqueous gelatino silver halide emulsion can adhere thereto on one side thereof, but which does not have a gelatin or any other proteinacious layer on the prepared side, then coating on the prepared side of the web by a continuous web coating method a layer of an aqueous solution which comprises from 0.5 to 2.0% by weight of agarose and from 0.5 to 3.0% by weight of a non-crossed-linked polyacrylamide or polyvinyl alcohol or a mixture of these polymers, at a temperature of at least 40° C., drying the coated layer to provide a dried layer having a thickness between 0.1 and 100 μm and comprising 10 to 50% by weight solids, and cutting the coated web into strips of the required size.

4. A method according to claim 3 wherein the thickness of the dried layer is from 5.0 to 15.0 μm.

5. A method according to claim 3 wherein the polyacrylamide used comprises a straight chain polyacrylamide having a molecular weight below 100,000 together with a minor proportion of a straight chain polyacrylamide having a molecular weight over 400,000 to increase the viscosity of the coating solution.

6. A method according to claim 5 wherein the polyacrylamide used comprises a straight chain polyacrylamide having a molecular weight of from 30.000 to 100.000 together with a minor proportion of a straight chain polyacrylamide having a molecular weight of from 400.000 to 600.000.

7. A method acording to claim 3 wherein the web material is a web of polyethylene laminated paper, the side of which is to be coated has been corona discharge treated.

8. A method according to claim 3 wherein the web material is biaxially orientated polyester which has been prepared by a process of orientating in one direction a web of unorientated polyester, applying to one surface of the polyester a copolymer latex completing the orientation and heat setting the attached polyester.

9. A method according to claim 8 wherein the copolymer comprises up to 10% by weight of itaconic acid.

10. A method according to claim 8 wherein the copolymer is a styrene based copolymer.

11. A method according to claim 8 wherein the polyester web after biaxial orientation is corona discharge treated on one side coated with the copolymer.

12. A method according to claim 3 wherein aqueous agarose and polymer solution is coated onto the web using a slot, trough, cascade or curtain coating machine.

13. A method according to claim 3 wherein a wetting agent is added to the aqueous agarose and polymer coating solution.

14. A method according to claim 3 wherein a swelling agent is added to the aqueous agarose and polymer solution.

15. A method according to claim 3 wherein an ampholyte is added to the aqueous agarose and polymer solution.

16. A diagnostic strip coated with agarose and polymer when prepared by the method claimed in claim 3.

* * * * *